United States Patent
Wösle

(10) Patent No.: US 11,986,675 B2
(45) Date of Patent: May 21, 2024

(54) METHOD FOR REAL-TIME CORRECTION OF A SPATIAL POSITION OF A CENTRAL BEAM OF RADIATION THERAPY DEVICES AND OF A PATIENT POSITION

(71) Applicant: STÄDTISCHES KLINIKUM DESSAU, Dessau-Roßlau (DE)

(72) Inventor: Markus Wösle, Dessau-Roßlau (DE)

(73) Assignee: STÄDTISCHES KLINIKUM DESSAU, Dessau-Roßlau (DE)

( * ) Notice: Subject to any disclaimer, the term of this patent is extended or adjusted under 35 U.S.C. 154(b) by 462 days.

(21) Appl. No.: 17/286,808

(22) PCT Filed: Nov. 6, 2019

(86) PCT No.: PCT/DE2019/000291
§ 371 (c)(1),
(2) Date: Apr. 19, 2021

(87) PCT Pub. No.: WO2020/094167
PCT Pub. Date: May 14, 2020

(65) Prior Publication Data
US 2021/0353965 A1 Nov. 18, 2021

(30) Foreign Application Priority Data
Nov. 9, 2018 (DE) ...................... 10 2018 008 806.6

(51) Int. Cl.
*A61N 5/10* (2006.01)

(52) U.S. Cl.
CPC ........... *A61N 5/1064* (2013.01); *A61N 5/103* (2013.01); *A61N 5/1045* (2013.01);
(Continued)

(58) Field of Classification Search
CPC ........ A61N 5/10; A61N 5/103; A61N 5/1036; A61N 5/1042; A61N 5/1045;
(Continued)

(56) References Cited

U.S. PATENT DOCUMENTS

| | | | |
|---|---|---|---|
| 5,189,687 A | 2/1993 | Bova et al. | |
| 5,278,886 A * | 1/1994 | Kobiki | A61N 5/1049 378/65 |

(Continued)

FOREIGN PATENT DOCUMENTS

| | | |
|---|---|---|
| DE | 10147633 A1 | 7/2002 |
| DE | 102010041752 A1 | 4/2012 |

(Continued)

OTHER PUBLICATIONS

Du, Weiliang et.al: Quantifying the gantry sag on linear accelerators and introducing an MLC-based compensation strategy. In: Medical Physics, vol. 39, 2012, No. 4, S. 2156-2162.—ISSN 0094-2405 (P); 2473-4209 (E).

*Primary Examiner* — Allen C. Ho
(74) *Attorney, Agent, or Firm* — Smartpat PLC

(57) ABSTRACT

A method provides real-time correction of the spatial position of the central beam of radiation therapy devices and therapy simulators, along with the patient position. In particular, the method relates to the real-time correction of irradiation positions of the collimator and/or the position of the patient positioning table during the performance of radiation therapy or therapy simulation. Positional deviations of the central beam of existing radiation therapy devices are reduced. Position adjustments of the collimator elements and/or of the patient support table are carried out through functional connections of separate control modules via separate adjustment devices. Those are added to the collimator and/or patient support table. Calculation of the correction movements takes place outside the radiation (Continued)

therapy device in the irradiation planning system and/or in at least one microcontroller of the control system of the radiation therapy device.

15 Claims, 7 Drawing Sheets

(52) U.S. Cl.
CPC ......... *A61N 5/1047* (2013.01); *A61N 5/1048* (2013.01); *A61N 5/1049* (2013.01); *A61N 5/1067* (2013.01); *A61N 5/107* (2013.01)

(58) Field of Classification Search
CPC .. A61N 5/1047; A61N 5/1048; A61N 5/1049; A61N 5/1064; A61N 5/1065; A61N 5/1067; A61N 5/1069; A61N 5/107; A61N 5/1071; A61N 2005/1072; A61N 2005/1074; G21K 1/02; G21K 1/04; G21K 1/043; G21K 1/046
USPC ........................................... 378/65, 150–153
See application file for complete search history.

(56) References Cited

U.S. PATENT DOCUMENTS

| | | | | |
|---|---|---|---|---|
| 5,446,548 | A * | 8/1995 | Gerig | A61B 6/08 250/462.1 |
| 6,760,402 | B2 * | 7/2004 | Ghelmansarai | A61B 6/583 378/65 |
| 6,804,548 | B2 * | 10/2004 | Takahashi | A61N 5/1049 378/65 |
| 6,956,196 | B2 * | 10/2005 | Duhon | G01S 17/36 250/221 |
| 6,999,556 | B2 * | 2/2006 | Nakano | A61N 5/103 378/65 |
| 7,085,347 | B2 * | 8/2006 | Mihara | A61N 5/10 378/65 |
| 7,154,991 | B2 * | 12/2006 | Earnst | A61B 6/548 378/65 |
| 7,239,684 | B2 * | 7/2007 | Hara | A61N 5/1049 378/65 |
| 7,469,035 | B2 * | 12/2008 | Keall | A61N 5/1042 378/65 |
| 7,839,972 | B2 * | 11/2010 | Ruchala | A61N 5/1048 378/65 |
| 7,860,550 | B2 * | 12/2010 | Saracen | A61B 6/548 5/601 |
| 7,907,987 | B2 * | 3/2011 | Dempsey | G01R 33/381 378/65 |
| 8,042,209 | B2 * | 10/2011 | D'Souza | A61N 5/1049 5/610 |
| 8,130,905 | B1 | 3/2012 | Nelms | |
| 8,189,738 | B2 * | 5/2012 | Dussault | A61N 5/103 378/65 |
| 8,229,068 | B2 * | 7/2012 | Lu | A61N 5/1049 378/65 |
| 8,295,435 | B2 * | 10/2012 | Wang | G06T 7/33 378/65 |
| 8,471,222 | B2 * | 6/2013 | Handa | G06F 18/00 378/65 |
| 8,767,917 | B2 * | 7/2014 | Ruchala | G16H 50/50 378/65 |
| 8,907,308 | B2 * | 12/2014 | Gliessmann | A61N 5/1049 250/397 |
| 8,989,350 | B2 * | 3/2015 | Shibuya | A61N 5/1065 378/65 |
| 9,089,696 | B2 * | 7/2015 | Verhaegen | A61N 5/1047 |
| 9,192,786 | B2 * | 11/2015 | Yan | A61N 5/1049 |
| 9,220,919 | B2 * | 12/2015 | Masumoto | A61N 5/1049 |
| 9,557,158 | B2 * | 1/2017 | Hofmann | A61B 6/0492 |
| 9,566,039 | B2 * | 2/2017 | Umekawa | A61B 6/0487 |
| 9,616,251 | B2 * | 4/2017 | Filiberti | A61N 5/107 |
| 9,974,977 | B2 * | 5/2018 | Lachaine | G06T 7/337 |
| 9,999,786 | B2 * | 6/2018 | Yoshimizu | A61N 5/1065 |
| 10,518,110 | B1 * | 12/2019 | Jimenez-Carvajal | A61N 5/1075 |
| 10,646,189 | B2 * | 5/2020 | Jin | A61B 6/542 |
| 10,940,331 | B2 * | 3/2021 | Mori | A61N 5/1064 |
| 11,065,472 | B2 * | 7/2021 | Ma | A61N 5/1048 |
| 11,247,074 | B2 * | 2/2022 | Wiersma | A61G 13/04 |
| 2002/0077545 | A1 | 6/2002 | Takahashi et al. | |
| 2005/0197564 | A1 | 9/2005 | Dempsey | |
| 2005/0228255 | A1 | 10/2005 | Saracen et al. | |
| 2010/0119032 | A1 | 5/2010 | Yan et al. | |
| 2012/0105969 | A1 | 5/2012 | Ehringfeld et al. | |
| 2013/0243157 | A1 | 9/2013 | Gliessmann | |
| 2014/0235921 | A1 | 8/2014 | Wendler et al. | |
| 2014/0288349 | A1 | 9/2014 | Seeber et al. | |
| 2015/0159994 | A1 | 6/2015 | Hofmann et al. | |
| 2016/0136459 | A1 | 5/2016 | Verhaegen et al. | |
| 2019/0021600 | A1 | 1/2019 | Grodzki et al. | |

FOREIGN PATENT DOCUMENTS

| | | |
|---|---|---|
| DE | 102011082257 | 8/2016 |
| DE | 202012013430 U1 | 1/2017 |
| DE | 102017212553 A1 | 1/2019 |
| EP | 1740098 A2 | 10/2005 |
| EP | 2883568 A1 | 6/2015 |
| WO | 8905171 A2 | 6/1989 |
| WO | 2013041720 A1 | 3/2013 |

* cited by examiner

METHOD FOR REAL-TIME CORRECTION OF A SPATIAL POSITION OF A CENTRAL BEAM OF RADIATION THERAPY DEVICES AND OF A PATIENT POSITION

TECHNICAL FIELD

The disclosure relates to a method for the real-time correction of the spatial position of the central beam of radiation therapy devices and therapy simulators, along with the patient position. In particular, the method relates to the real-time correction of irradiation positions of the collimator and/or the position of the patient positioning table during the performance of radiation therapy or therapy simulation. Instead of the irradiation positions of the collimator, the irradiation position of the radiation source can also be corrected. The method is preferably used for precise irradiation methods such as stereotactic radiotherapy and radiosurgery; however, it can be applied to any irradiation technique and to therapy simulation.

BACKGROUND

Solutions that relate to the determination of the position of objects in an irradiation room are generally known. For example, according to EP 2 883 568 A1, a system and method for determining the position of objects in an irradiation room is presented. For this purpose, room lasers are arranged in the irradiation room, which room lasers project at least one laser line onto the surface of a patient located on a patient table. At least one camera is then used to record the laser lines projected onto the surface of the patient. The cameras are followed by an evaluation and control device that, during an irradiation process, determines the coordinate points of the projected laser line on the basis of the measured values recorded by the camera by means of a real-time triangulation process. The determined coordinate points are compared with target coordinate points and the values obtained are stored. The stored values are used to document the irradiation process.

Another solution according to DE 101 47 633 A1 relates to a system and a monitoring method for detecting the irradiation target, its position and the movement of the irradiation target. This proposed system is intended to reduce the stress on the patient caused by the head ring and mouthpiece required in the process. On the other hand, precise radiation therapy is to be made possible not only in the head area, but also in the torso area. In addition, the therapy should not require a positioning frame for the irradiation target. Among other things, a real-time imaging device is used to capture high-resolution 3D images of the irradiation target area. Using an irradiation condition correction device, the position and direction of the irradiation target areas are changed in real time based on the acquired images.

In another solution according to DE 10 2010 041 752 B4, a method for calibrating a leaf collimator and a computer program required for this purpose are described. Such collimators comprise a plurality of leaves, which are independently movable. The radiation area can be flexibly adjusted in this manner, limiting the beam to the affected tissue to be irradiated. With the presented method, the geometric calibration of the entire system consisting of leaves and leaf carriers is made less time-consuming. This is achieved by determining the positional deviations for the leaves through a direct application of imaging techniques. The position deviations of the leaf carrier can be determined without explicit measurements. By recording the leaves and comparing the recording with a reference image, deviations of the leaf positions are determined.

According to WO 2013/041720 A1, a system and method for positioning patients using nuclear imaging are further known. For this purpose, the position of radioactively marked target tissue of patients is determined. Depending on measurement data from a nuclear radiation detector, a device is then used to adjust the relative position of the patient to a radiation source. In doing so, the precise recording of the target structure is necessary to minimize damage to the healthy surrounding tissue. By means of the detector system and a downstream computational processing of the recorded detector signals, information regarding the size, position and shape of the target tissue in space is determined. By comparing such data with the geometric data of the radiation path of the irradiation device, it is possible to determine how the position of the patient must be changed. In the simplest case, the correction variable represents a three-dimensional vector whose length and direction indicate the change required for irradiation to begin.

EP 1 740 098 B1 describes a patient positioning assembly that is designed as a robotic device and is used to support and move the accommodated patient. The robotic device to be used is capable of moving the patient in at least five degrees of freedom. For this purpose, the device has an arm assembly, which is coupled to the treatment table in order to move the treatment table through three rotational degrees of freedom along with three translational degrees of freedom. A sensor system is used to detect the position of the robot device relative to the treatment coordinate system. For this purpose, near real-time data of the treatment target and information regarding the position of the therapeutic radiation source are used and the displacement of the robotic device is controlled. By means of the control system, the treatment target is aligned according to the position of the therapeutic radiation source.

The subject matter disclosed according to DE 20 2012 013 430 U1 relates to a therapeutic device for treating a predetermined body part of a patient with radiation. The method used likewise serves to control the therapeutic device using a real-time system. The assemblies of the real-time system connected to the positioning system of the treatment table, the radiation positioning system and the collimator are designed to be programmable.

Furthermore, according to DE 10 2011 082 257 B4, a radiation therapy device with an irradiation field limiting device, which comprises a multi-leaf collimator (MLC) for adjusting the irradiation field, a patient table and a verification device for visually verifying the irradiation field, has become known from the prior art. In this regard, the verification device is designed to visually display the irradiation field on a patient. The patient, positioned at a distance from the isocenter of the radiation therapy device, is in a virtual isocenter for this purpose. By means of the patient table, the patient is brought into position from the virtual isocenter in the isocenter of the radiation therapy device. The virtual isocenter of the radiation therapy device and a projection of the radiation field are thereby combined with one another and in this manner an optimization of the workflow within radiation oncology is achieved.

All of the solutions described above are intended for the manufacture and application of completely redesigned radiation therapy devices with the associated high acquisition costs. None of the methods in the patents described above, in contrast to the method mentioned at the beginning, correct central beam deviations of the radiation therapy device caused by mechanical tolerances and elastic deformations due to dead weight. The patents cited above consider the isocenter of a radiation therapy device to be point-like, although it always has a spatial extension.

With many medical electron linear accelerators in clinical use, the deflection of the support arm due to dead weight along with isocentric rotations of the patient support table due to mechanical tolerances lead to spatial central beam displacements relative to the tumor center. The largest component of the central beam displacement in the Y-direction in terms of magnitude is regularly caused by the elastic deformation of the support arm that holds the radiator head; this phenomenon is called "gantry sag" in the technical literature. By increasing the stiffness of the support arm structures, attempts to minimize central beam displacements have been made up to now. For example, improved designs of the support arm and support arm bearing in terms of stiffness are available from all manufacturers of radiation therapy devices at an additional cost. According to the specifications of the linear accelerator manufacturers, the global isocentroid (the isocenter with a spatial extension) has a maximum diameter of 1.5 mm with these improved support arm structures. For standard designs, the maximum diameter amounts to 2 mm.

In the case of precise radiation techniques such as stereotactic radiotherapy or stereotactic radiosurgery of disease foci in the immediate vicinity of
   radiation-sensitive serial organs that are vital, such as the brain stem and spinal cord, or
   organs that enable organ-preserving therapy through their preservation of function, such as a lacrimal gland in organ-preserving eye tumor therapy,
the treating physician regularly wants a radiation therapy device with an ideal isocenter. This would enable him to increase local tumor control probabilities with reduced organ toxicities by requiring less irradiation of healthy tissue.

SUMMARY

As such, an object of the disclosure is to provide a method with which the positional deviations of the central beam of existing radiation therapy devices are reduced, and the technical effort required for accuracy and patient comfort is optimized.

This object is achieved with the method as claimed.

As illustrated in FIG. 7, the increase in the real-time related accuracy of the central beam is achieved by controlling the spatial positions of the collimator elements (block apertures, leaves, leaf carriers, round collimators) or the components of the radiation source, and/or the patient positioning table for optional additional degrees of freedom of the correction movements. The optimum technical effort is achieved through functional connections of separate control modules to the control equipment of existing radiation therapy devices. The use of separate adjustment devices is advantageous for reducing the material and technical expenditure for changing the spatial positions of the collimator elements or the radiation source, and/or the patient positioning table within the optional additional degrees of freedom. For this purpose, the separate adjustment devices are connected to the collimator or the radiation source, and/or the patient positioning table via the respective control modules. The technical and cost effort for the control of the spatial position is effectively reduced if the control is carried out by a control module, which is designed as a microcontroller, which contains a computer program controlling the adjustment devices. The optimization of the control system of already existing radiation therapy devices is effectively achieved if, by means of the connectable control modules, the control of the collimator elements in the X and Y directions of the collimator-fixed coordinate system or of the radiation source components in the X and Y directions of the source-fixed coordinate system, as the case may be, and/or of the patient positioning table is carried out within the degrees of freedom in all three spatial directions of the table-fixed coordinate system. In order to achieve high positioning accuracy and maximum patient comfort, the control within the degrees of freedom in the X and Y directions is preferably limited to the real-time related position changes of the collimator elements. Minimal costs by avoiding the redesign of additional degrees of freedom are effectively achieved if the control within the degrees of freedom in the X, Y and Z directions is limited to the real-time related position change of the patient positioning table. Depending on the defined optimization goal
   maximum patient comfort with the table top unmoved,
   minimal costs of redesign or retrofitting,
   minimum effective residual deviation of the central beam relative to the center of the disease focus,
   maximum geometric stability of the central beam over time, or
   minimal time required for verifications and recalibrations
   the control of the radiation therapy device can perform any combination of the real-time position changes of the collimator elements, the radiation source components and the patient positioning table.

BRIEF DESCRIPTION OF THE DRAWINGS

In the following, the invention will be explained in more detail with reference to an exemplary embodiment.

DETAILED DESCRIPTION

Figure 1:
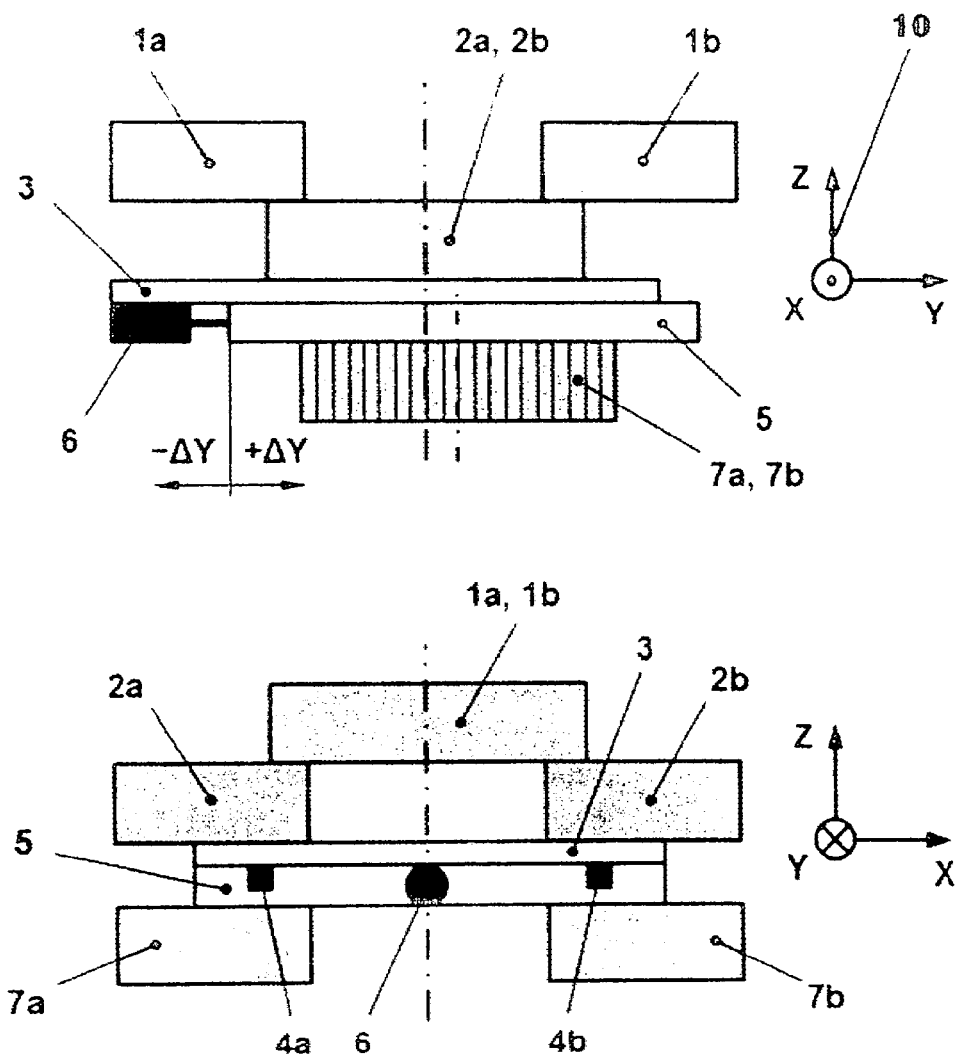
FIG. 1 shows a redesign of the degree of freedom in the Y direction for the multi-leaf collimator.

A typical support arm structure made of steel of a linear accelerator consists of at least two welded parts, which are screwed to one another to form an L-shaped support arm. The preferred profile shape is U-shaped with a high bar; the profiles are arranged in pairs. As a result, the space between the profiles has a rectangular cross-section in which numerous electrical, electronic and physical assemblies for beam generation, energy selection, beam shaping and dose rate control are housed. The rotatable support arm itself is mounted in the stand of the radiation therapy device via a preloaded four-point deep groove ball bearing. Improvements to the predominate support arm structure described below are based on an analysis of the elastic deflection of a beam that is firmly fixed on one side and statically loaded by a line load that corresponds to its dead weight This is a simple model for a support arm. According to [1], the angle of inclination is then $$\alpha_x = \frac{q_z \cdot L^3}{6 \cdot E \cdot I_n} = \frac{m' \cdot g \cdot L^3}{6 \cdot E \cdot I_x} = \frac{\rho \cdot V \cdot g \cdot L^2}{6 \cdot E \cdot I_x} \quad (1)$$

about the bending axis in the transverse direction x at the free end, which is directly proportional to an associated central beam displacement perpendicular to the bending axis. Thus, in accordance with equation (1), the central beam displacement is proportional to the line load $q_x = m' \cdot g$ in the z direction, or to the mass m' per length, which is proportional to the physical density $\rho$, and to the third power of the beam length L and inversely proportional to the modulus of elasticity E of the material and to axial moment of area of the 2nd degree $I_x$ of the profile about the x axis. The constant g is the acceleration due to gravity in the gravitational field of the earth; V is the volume of the beam.

The following measures are useful for further reducing the angle of inclination $\alpha_x$:

Omission of all non-essential supporting screw connections to eliminate their setting amounts, which contribute to the elastic deformation of the support arm. Form-fit and force-fit screw connections, which have a high degree of rigidity, also have comparatively more mass than material-fit welded joints.

Increase in the bending stiffness of the support arm by improved shaping of the supporting profiles, without thereby increasing the overall height and the mass per length. That is, a profile for which the quotient $m'/I_x$ becomes minimal is sought. Here, narrow I-beams in accordance with DIN 1025—sheet 1 and medium-wide I-beams of the form IPE in accordance with DIN 1025—sheet 5 are better than U-channel in accordance with DIN 1026—sheet 1 or UPE channel in accordance with DIN 1026—sheet 2. For a profile height in the range of (260 . . . 270) mm, which is common in support arm structures, one would be able to increase the bending stiffness with I-beams compared to a U-profile by up to 7.7% with an almost unchanged weight per meter. The characteristic values of the steel beam sections used for this estimation are taken from Table 1.

num would be better here; its $\rho/E$ ratio is 18.3% lower, as shown in Table 2. This consideration is only theoretical, since molybdenum is much more expensive and difficult to process than steel. The price per kilogram of semi-finished molybdenum products is higher by a factor of 100 . . . 240. No high-strength welds can be produced; however, brazing is possible. Other materials with a high modulus of elasticity, such as nickel and tungsten, are not useful in this estimation from a purely mechanical point of view (see values for $\rho/E$ in Table 2).

TABLE 2

| Material | $\rho \left[\frac{kg}{dm^3}\right]$ | $E \left[\frac{N}{mm^2}\right]$ | $\frac{\rho}{E} \left[\frac{g \cdot mm^2}{dm^3 \cdot N}\right]$ | $\left(\frac{\rho}{E}\right)_{rel}$ [1] |
|---|---|---|---|---|
| Steel | 7.95 | 210000 | 0.038 | 1.000 |
| Nickel | 8.8 | 210000 | 0.042 | 1.107 |
| Molybdenum | 10.21 | 330000 | 0.031 | 0.817 |
| Tungsten | 19.3 | 390000 | 0.049 | 1.307 |

Physical density $\rho$ and modulus of elasticity E of a set of materials from [1] for the design of bend-resistant supporting structures, where $(\rho/E)_{rel}$ is the material parameter relative to steel.

Since the rigidity of the support arm bearing also influences the central beam displacement, the single row deep groove ball bearing would be replaced by a double-row tapered roller bearing in an X or O arrangement. From a designer's point of view, the O arrangement would be preferred here, since it has less tilting clearance and is therefore more rigid than an X arrangement. The paired bearing arrangements considerably increase the static and dynamic rigidity of a rolling bearing arrangement. In addition, due to the line contact between the tapered rolling elements and the ball races, the Hertzian pressure is lower and the bearing rigidity is higher than in the case of point contact of spherical rolling elements. The load ratings of such rolling bearing types with a respective bore diameter in the order of magnitude of the support arm bearings actually used in Table 3 demonstrate this. With unchanged bearing forces and torques, an increase in bearing stiffness by a factor of 7.5 to 8.7 would be possible. This is a rough estimate using the ratios of the static load ratings. The static load rating of a rolling bearing corresponds to the static bearing force at which permanent deformations occur at the

TABLE 1

| Profile | H [mm] | $m' \left[\frac{kg}{m}\right]$ | $I_x$ [cm⁴] | $\frac{m'}{I_x} \left[\frac{g}{m \cdot cm^4}\right]$ | $\left(\frac{m'}{I_x}\right)_{rel}$ [1] | DIN |
|---|---|---|---|---|---|---|
| U | 260 | 37.9 | 4820 | 7.863 | 1.077 | 1026 – 1 |
| I | 260 | 41.9 | 5740 | 7.300 | 1.000 | 1025 – 1 |
| UPE | 270 | 35.2 | 5255 | 6.698 | 1.074 | 1026 – 2 |
| IPE | 270 | 36.1 | 5790 | 6.235 | 1.000 | 1025 – 5 |

Physical and strength characteristics of a set of hot rolled steel beam sections from [I] (U = U-steel, I = narrow I-beam, UPE = U-steel with parallel flanks, IPE = medium width I-beam, H = total height, m' = mass per length, $I_x$ = 2nd degree axial moment of area about the transverse axis x, $(m'/I_x)_{rel}$ = characteristic value of U-steel relative to corresponding I-beam).

In addition to the geometry, the material properties can also be optimized, so that the quotient m'/E or $\rho/E$, as the case may be, becomes minimal. Instead of steel, molybdecontact points between the rolling elements and the ball races which are less than or equal to $10^{-4}$ times the rolling element diameter.

TABLE 3

Bore diameter d, outside diameter D, bearing width B, static load rating $C_0$,
static load rating $C_{0,rel}$ relative to deep groove ball bearings and mass m of various rolling
bearing designs of SKF GmbH, Schweinfurt, Germany

| Bearing Type | d [mm] | D [mm] | B [mm] | $C_0$ [kN] | $C_{0,rel}$ [l] | m [kg] | Design | Arrangement |
|---|---|---|---|---|---|---|---|---|
| Deep groove ball bearing 1 | 710.0 | 950.0 | 78.0 | 1290 | 1.000 | 167 | single row | — |
| Tapered roller bearing 2 | 711.2 | 914.4 | 190.5 | 9650 | 7.481 | 265 | dual row | TDO |
| Tapered roller bearing 3 | 660.4 | 812.8 | 176.2 | 11200 | 8.682 | 195 | dual row | TDI |

(TDO = O arrangement,
TDI = X arrangement;
bearing abbreviations: [1]609/710 MA, [2]BT2B 328028/HA1 [3]331198).

If one wanted to improve the bending stiffness of a support arm structure even more, the shape of the supporting steel profiles along with the roller bearings of the supporting arm should be changed. The supporting structure of the support arm should be manufactured as a welded part without screw connections.

The resulting gain in stiffness with improved bearing and support arm stiffness is greatly reduced by the series arrangement of both stiffnesses. The total stiffness $c_{ges}$ can be determined in accordance with the equation $$\frac{1}{c_{ges}} = \frac{1}{c_1} + \frac{1}{c_2} \quad (2)$$

from the individual stiffnesses $c_1$ and $c_2$. This gives the relative total stiffness before improvement at 0.5 with the basic relative stiffnesses $c_1 = c_2 = 1$, assuming that the absolute individual stiffnesses are of the same order of magnitude. With the relative increases in stiffness $c_1 = 7.5$ and $c_2 = 1.077$ due to the double-row tapered roller bearing in O arrangement and the use of narrow I-beams in the support arm structure, as the case may be, the relative overall stiffness would be 0.941. With the design improvements, the deflection of the support arm under dead weight and thus the central beam displacement could at best be halved, as specified by the quotient $c_{ges|vorher}/c_{ges|nachher} = 0.5/0.941 = 0.531$.

An attempted solution for geometric central beam correction is described by the authors of the publication [2], by measuring the isocentroid of the support arm for a full rotation. They only use the central beam deviations in the Y direction, which are dependent on the support arm angle, in order to be able to reduce the isocentroid in this direction only. Subsequently, the leaf positions of the multi-leaf collimator, which are dependent on the support arm angle, are corrected for the central beam deviations, offline (in the irradiation planning system). In doing so, the collimator angle must be set to a constant 90°. In this manner, tumors in patients cannot be optimally irradiated, since the optimal collimator angle depends on the direction of irradiation.

With the hardware solutions to reduce the mechanical central beam displacements, the support arms and support arm bearings of electron linear accelerators are built to be stiffer. However, one is limited in the installation space. In addition, an increase in stiffness with the traditional mechanical engineering material steel is only possible to a limited extent by shaping, such that one is confronted with an increase in the dead weight; here, over 7 t has now been reached. However, the support arm and support arm bearing stiffness, which together with the large moving mass principally cause the central beam position deviations, always remain finite.

With the invention, it is possible to follow the prior art, with which the central beam position deviations are more or less reduced by stiffening the support arm and/or the support arm bearing in the stand. By means of measurements, calculations along with control and regulation algorithms, the remaining central beam position deviations are to be further reduced or compensated for, if the tolerance widths and reproducibility of the actuators of the radiation therapy device permit this.

Since precision in engineering is expensive, the invention enables one to make a stereotactic radiation therapy device out of any standard radiation therapy device that has a less rigid support arm than a stereotactic radiation therapy device. Thus, the further development of stiffer support arm structures is obsolete. With the aid of the invention, geometrically precise radiation therapy devices can be manufactured more cost-effectively, since constructive measures to increase the rigidity of the support arm can go in the opposite direction: In the future, it will be possible to make the entire support arm structure lighter and to allow greater geometric deviations of the central beam than before. In addition to the cost savings, fewer problems would be expected in bringing in and assembling the heavy machine parts on site, since permissible ceiling loads and clear widths of access routes in existing buildings are often limited.

There are two paths to corrected irradiation geometry:

1. One takes the real central beam, which deviates from its ideal position, to the ideal isocenter.
2. One takes the center of the disease focus with the patient to the piercing point of the real central beam in the isocenter plane.

Both methods can also be combined (depending on the defined optimization goal, see above). As a result, one always obtains the best possible irradiation geometry that is possible within the remaining tolerance widths and finite reproducibility of the actuators of the radiation therapy device.

Carrying Out the Central Beam Position Correction

The spatial central beam deviation relative to the measuring body, which indicates the ideal isocenter in the Winston-Lutz test, in the inertial frame $I = \{ISO, X, Y, Z\}$ is contained in the vector $$_I\Gamma_{ISO}(K) = \begin{pmatrix} _IX_{ISO}(K) \\ _IY_{ISO}(K) \\ _IZ_{ISO}(K) \end{pmatrix} \in \mathbb{R}^3 \qquad (3)$$

Equation (3) applies to the three angles $K \in \{G, C, T\}$ of the support arm, collimator and patient positioning table. The coordinate axes are defined as follows:

X points from left to right as viewed from the foot end of the patient positioning table top, Y points in the longitudinal direction of the patient support table top in the direction of the support arm bearing and Z points from the floor towards the ceiling of the irradiation room.

The vector in equation (3) describes the isocentroid completely. It is initially calculated in the plane of the electronic portal imaging device (EPID), which is used for the measurement, in the EPID coordinate system there in accordance with $$_{EPID}r_{ISO} = {}_{EPID}r_{CAX} - {}_{EPID}r_{MK} \qquad (4)$$

from the position vectors r of the central beam CAX and of the measuring body MK. The mapping matrices $$A_\beta = \begin{pmatrix} \cos\beta & 0 & \sin\beta \\ 0 & 1 & 0 \\ -\sin\beta & 0 & \cos\beta \end{pmatrix} \in \mathbb{R}^{3,3} \text{ and} \qquad (5)$$

$$A_\gamma = \begin{pmatrix} \cos\gamma & -\sin\gamma & 0 \\ \sin\gamma & \cos\gamma & 0 \\ 0 & 0 & 1 \end{pmatrix} \in \mathbb{R}^{3,3} \qquad (6)$$

and their inverse matrices, which are needed in the following to get from body-fixed coordinate systems rotated around the Y axis or Z axis to the space-fixed inertial system and vice versa, can be taken from the book [3]. Thereby, $\beta$ and $\gamma$ are the signed angles of rotation about the Y and Z axes, as the case may be. The measurement is performed with a sufficiently small angular increment for all three angular degrees of freedom G, C, and T. To generate a closed characteristic diagram for describing the global central beam deviations, nonlinear interpolation is performed between angular steps, for example by means of cubic splines or piece by piece by means of cubic Hermite interpolation. Ideally, the angular ranges of G, C and T are traversed continuously at a constant angular velocity. In such a case, the interpolations are omitted.

Since the isocentroids of a radiation therapy device are further dependent on the parameters of type of radiation, particle energy and type of collimation such a characteristic diagram must be determined by measurement for each combination of such parameters used for patient irradiation. For a typical electron linear accelerator in photon mode, which can generate four particle energies and allows three collimation modes, twelve characteristic diagrams would have to be included.

In order for the measurement results to be representative of an elastic support arm and thus reproducible, the relaxation of the support arm due to elastic deformations, setting amounts as well as the tribology in the grease-lubricated support arm rolling bearing must be effectively counteracted. This requires a movement program for the support arm, which it must go through before starting a precision measurement of the isocentroid geometry:

Preparation of the measurement at the support arm angle G=0°. In this angular position, the measuring body is mounted on the patient positioning table and adjusted by means of the room-fixed lasers or by means of a radiological patient positioning system, which is independent of the radiation therapy device.

The support arm must now complete 3½ full rotations before the measurement of the support arm isocentroid begins.

Before the measurement of the collimator isocentroid takes place, the support arm must rest for 5 min at the angular position 0°.

Subsequently, the support arm must also rest for 5 min each at the angular positions −30° and 30° before the left-sided and right-sided parts of the patient positioning table isocentroid can be determined.

This allows reproducible isocentroids to be obtained, independent of the device, which differ in size and position by no more than 0.02 mm, even if the support arm has remained in a certain resting position at night or over a weekend.

Now, the steps of the central beam correction in detail:

1. Determination of the size and position of all isocentroids as a function of support arm, collimator and table angle, as the case may be. The block apertures, leaves and round collimators, as the case may be, are each in the nominal position, that is, they are in their nominal positions of the irradiation planning, to which no position corrections have yet been applied. The support arm isocentroid results in $$_Ir_{ISO}(G) = A_\beta \cdot k^{-1} \cdot {}_{EPID}r_{ISO}(G). \qquad (7)$$

The collimator isocentroid results in $$_Ir_{ISO}(C) = A_\gamma \cdot k^{-1} \cdot {}_{EPID}r_{ISO}(C). \qquad (8)$$

The patient positioning table isocentroid results in $$_Ir_{ISO}(T) = A_\beta \cdot k^{-1} \cdot {}_{EPID}r_{ISO}(G,T). \qquad (9)$$

Here, $\beta = G$, $\gamma = C$ and $$k = \frac{SID}{SAD} > 1, \qquad (10)$$

where SID is the adjusted focus EPID distance and SAD is the fixed focus ISO distance.

2. Composition of the global characteristic diagram for all angle-dependent central beam deviations relative to the measuring body:

$$_Ir_{ISO}(G,C,T) = {}_Ir_{ISO}(G) + [{}_Ir_{ISO}(C) - {}_Ir_{ISO}(C_0)] + [{}_Ir_{ISO}(T) - {}_Ir_{ISO}(T_D)]. \qquad (11)$$

Here, $C_0 = 0°$ and $T_0 = 0°$ are the collimator and table angle positions for measuring the support arm isocentroid.

3. Mapping of the global characteristic diagram into the collimator-fixed coordinate system C:

$$_Cr_{ISO}(G,C,T) = A_\gamma^{-1} \cdot A_\beta^{-1} \cdot {}_Ir_{ISO}(G,C,T). \qquad (12)$$

Here, $\gamma = C$ and $\beta = G$.

4. Projection of the characteristic diagram into the plane of the upper Y block aperture pair, also referred to as upper jaws (UJ):

$$_c\Gamma_{UJ}(G,C,T) = \begin{pmatrix} c\Delta X_{UJ}(G,C,T) \\ c\Delta Y_{UJ}(G,C,T) \\ c\Delta Z_{UJ}(G,C,T) \end{pmatrix} = k_{UJ}^{-1} \cdot {_c\Gamma_{ISO}}(G,C,T), \quad (13)$$

where the stretch factor $$k_{UJ} = \frac{SAD}{SYD} > 1 \quad (14)$$

depends on the focus Y aperture distance SYD.

5. Projection of the characteristic diagram into the plane of the lower X block aperture pair, also referred to as lower jaws (LJ):

$$_c r_{LJ}(G,C,T) = \begin{pmatrix} c\Delta X_{LJ}(G,C,T) \\ c\Delta Y_{LJ}(G,C,T) \\ c\Delta Z_{LJ}(G,C,T) \end{pmatrix} = k_{LJ}^{-1} \cdot {_c r_{ISO}}(G,C,T), \quad (15)$$

where the stretch factor $$k_{LJ} = \frac{SAD}{SXD} > 1 \quad (16)$$

depends on the focus X aperture distance SXD.

6. Projection of the characteristic diagram into the plane of the multi-leaf collimator (MLC):

$$_c r_{MLC}(G,C,T) = \begin{pmatrix} c\Delta X_{MLC}(G,C,T) \\ c\Delta Y_{MLC}(G,C,T) \\ c\Delta Z_{MLC}(G,C,T) \end{pmatrix} = k_{MLC}^{-1} \cdot {_c r_{ISO}}(G,C,T), \quad (17)$$

where the stretch factor $$k_{MLC} = \frac{SAD}{SMD} > 1 \quad (18)$$

depends on the focus MLC aperture distance SMD.

7. When using round collimators, steps 4 to 6 are omitted. The projection of the global characteristic diagram into the plane of the round collimator or circular cone (CC) is described by $$_c r_{CC}(G,T) = \begin{pmatrix} c\Delta X_{CC}(G,T) \\ c\Delta Y_{CC}(G,T) \\ c\Delta Z_{CC}(G,T) \end{pmatrix} = k_{CC}^{-1} \cdot {_c r_{ISO}}(G,C,=0°,T) \quad (19)$$

where the stretch factor $$k_{CC} = \frac{SAD}{SCD} > 1 \quad (20)$$

depends on the focus-cone distance SCD.

8. The position correction values $$\begin{pmatrix} c\Delta Y_{UJ}(G,C,T) \\ c\Delta X_{LJ}(G,C,T) \\ c\Delta X_{MLC}(G,C,T) \\ c\Delta Y_{MLC}(G,C,T) \end{pmatrix} \in \mathbb{R}^4 \quad (21)$$

from equations (13), (15) and (17), respectively, as the case may be, $$\begin{pmatrix} c\Delta X_{CC}(G,T) \\ c\Delta Y_{CC}(G,T) \end{pmatrix} \in \mathbb{R}^2 \quad (22)$$

from equation (19) are applied to all collimator position parameters used. However, the fourth correction term in equation (21) cannot be applied to any of the radiation therapy devices currently in clinical use with a multi-leaf collimator, since there is no degree of freedom for it. The same applies to the two correction terms in equation (22). Suitable redesigns to apply these correction terms are described below. Finally, one obtains the corrected positions of the block apertures in accordance with $$_c X_{LJ}(G,C,T) = {_c X_{LJ}}|_{RTP} - {_c\Delta X_{LJ}}(G,C,T), \quad (23)$$

$$_c Y_{UJ}(G,C,T) = {_c Y_{UJ}}|_{RTP} - {_c\Delta Y_{UJ}}(G,C,T), \quad (24)$$

of the multi-leaf collimator in accordance with $$_c X_{MLC}(G,C,T) = {_c X_{MLC}}|_{RTP} - {_c\Delta X_{MLC}}(G,C,T), \quad (25)$$

$$_c Y_{MLC}(G,C,T) = {_c Y_{MLC}}|_{RTP} - {_c\Delta Y_{MLC}}(G,C,T), \quad (26)$$

or of the round collimator used in accordance with $$_c X_{CC}(G,T) = {_c X_{CC}}|_{RTP} - {_c\Delta X_{CC}}(G,T), \quad (27)$$

$$_c Y_{CC}(G,T) = {_c Y_{CC}}|_{RTP} - {_c\Delta Y_{CC}}(G,T), \quad (28)$$

In equations (23) to (28), the summands $(\ldots)|_{RTP}$ are the target positions of the block apertures, the leaf packets and the round collimator, as the case may be, of a geometrically ideal radiation therapy device determined in the irradiation planning system. The corrections of the leaf positions are carried out in packets, that is, both carriages (leaf carriers) on which the leaves and their drives of the A and B side (positive and negative X direction in the coordinate system C) are arranged, carry out the correction displacements simultaneously. For an ideal radiation therapy device with a point-like isocenter, $_c Y_{MLC}|_{RTP}, {_c X_{CC}}|_{RTP}, {_c Y_{CC}}|_{RTP} = 0$ applies for the target positions.

9. Two strategies are conceivable for executing the correction movements by the collimator elements:

a. The angle-dependent correction movements in equations (21) and (22), as the case may be, are calculated offline in the irradiation planning system, defined by means of control points for the support arm angle-dependent (time-dependent) aperture and leaf positions and round collimator positions, as the case may be, and stored in the oncology information system. The computational time required for this is minor, since this process does not affect the duration of an irradiation session. When loading the irradiation parameters from the oncology information system, the radiation therapy device already receives the corrected support arm angle-dependent aperture and leaf positions or round collimator positions, as the case may be.

b. The angle-dependent correction movements are calculated online by the radiation therapy device after loading the irradiation parameters. For this purpose, the necessary displacements are read in real time from the characteristic diagrams of equations (13), (15) and (17) or (19) and applied to the current positions of the block apertures and the multi-leaf collimator or the round collimator used, as the case may be. A microprocessor with sufficient computing power is indispensable.

10. For verification of the respective correction, all three isocentroids are measured and analyzed once again.
11. The recording of the characteristic diagram for correction along with the verification of the correction are repeated at regular intervals to ensure patient safety, despite changing tolerance widths over the lifetime of the radiation therapy device.

Carrying Out the Position Correction of the Radiation Source

Instead of changing the positions of the collimator elements, the position of the radiation source can also be changed to correct the spatial central beam position. In the photon mode of a medical electron linear accelerator, the radiation source consists of the target and the compensating element, which lie with their respective centers in the central beam axis (coaxial) and are arranged one behind the other. Photons can also be applied to disease foci without a compensating element.

With this procedure, steps 3 to 8 are omitted from the central beam correction procedure described in the previous section and are replaced by the following steps:

3. Based on equation (11) under item 2 in the previous section, the mapping of the global characteristic diagram of the central beam deviations into the source-fixed coordinate system S results in $$_S r_{ISO}(G,C,T) = A_\beta^{-1} \cdot {}_I r_{ISO}(G,C,T) \quad (29)$$

with the angle of rotation $\beta = G$.

4. Projections of the global characteristic diagram into the planes of the radiation source components $S_i$ with $i \in \{\text{target, compensating element}\}$:

$$_S r_{S_i}(G,C,T) = \begin{pmatrix} {}_S \Delta X_{S_i}(G,C,T) \\ {}_S \Delta Y_{S_i}(G,C,T) \\ {}_S \Delta Z_{S_i}(G,C,T) \end{pmatrix} = k_{S_i} \cdot {}_S r_{ISO}(G,C,T), \quad (30)$$

where the stretch factors $$k_{S_i} = \frac{S_i AD}{S_i AD - S_i MD} \quad (31)$$

are functions of the distances $S_i AD$ and $S_i MD$ of the respective radiation source component Si from the isocenter ISO or from the MLC plane, as the case may be, if the multi-leaf collimator (MLC) is used for beam shaping. When using round collimators, the distance $S_i MD$ in equation (31) must be replaced by the distance to the round collimator plane $S_i CD$. Furthermore, when using the X and Y block apertures, the distances $S_i XD$ or $S_i YD$, as the case may be, to the respective aperture plane must be used. In this case, the stretch factors $k_{S_i}$ for the X and Y components of the vector in equation (30) differ.

5. The position correction values $$\begin{pmatrix} {}_S \Delta X_{S_i}(G,C,T) \\ {}_S \Delta Y_{S_i}(G,C,T) \end{pmatrix} \in \mathbb{R}^2 \quad (32)$$

arising from equation (30) are applied to the components of the radiation source. They usually have one degree of freedom in the X direction, which has a high positioning accuracy. However, the second correction term in equation (32) cannot be applied to any of the radiation therapy devices currently in clinical use, since no degree of freedom is provided for it. A suitable redesign to apply this correction term is described below. Finally, the corrected positions of the radiation source components are obtained with $$_S X_{S_i}(G,C,T) = {}_S X_{S_i}|_{RTP} + {}_S \Delta X_{S_i}(G,C,T), \quad (33)$$

$$_S Y_{S_i}(G,C,T) = {}_S Y_{S_i}|_{RTP} + {}_S \Delta Y_{S_i}(G,C,T), \quad (34)$$

For an ideal radiation therapy device with a point-like isocenter, $_S X_{Si}|_{RTP}, {}_S Y_{Si}|_{RTP} \equiv 0$ applies for the target positions.

Steps 1, 2 and 9 to 11 proceed exactly as outlined in the previous section.

Carrying Out the Patient Position Correction

To calculate the correction values for the translational degrees of freedom of the patient positioning table, the characteristic diagram in equation (11) is required. The correction process can be divided into four steps:

1. Using the inverse of the matrix in equation (6), we obtain table correction values in the table-fixed coordinate system T in accordance with $$_T r_T(G, C, T + \Delta T) = \begin{pmatrix} {}_T \Delta X_T(G, C, T + \Delta T) \\ {}_T \Delta Y_T(G, C, T + \Delta T) \\ {}_T \Delta Z_T(G, C, T + \Delta T) \end{pmatrix} \in \mathbb{R}^3 \quad (35)$$

$$_T r_T(G, C, T + \Delta T) = A_\gamma^{-1} \cdot {}_I r_{ISO}(G, C, T).$$

Here, the angle of rotation $\gamma = T + \Delta T$ corresponds to the current table angle. When using an external patient positioning system, a correction term $\Delta T \neq 0°$ is considered, which is otherwise $\Delta T = 0°$. The corrected translational coordinates of the patient positioning table are obtained in accordance with $$_T X_T(G,C,T+\Delta T) = {}_T X_T|_{RTP} - {}_C \Delta X_T(G,C,T+\Delta T), \quad (36)$$

$$_T Y_T(G,C,T+\Delta T) = {}_T Y_T|_{RTP} - {}_T \Delta Y_T(G,C,T+\Delta T), \quad (37)$$

$$_T Z_T(G,C,T+\Delta T) = {}_T Z_T|_{RTP} - {}_T \Delta Z_T(G,C,T+\Delta T), \quad (38)$$

2. For the execution of the correction movements by the patient positioning table, only an online variant can be considered, since the table coordinates are usually not constant over the individual irradiation sessions. Thus, the correction movements can usually not be determined in advance (offline) by the irradiation planning system.

3. For verification of the respective correction, all three isocentroids are measured and analyzed once again.
4. The recording of the characteristic diagram for correction along with the verification of the correction are repeated at regular intervals to ensure patient safety, despite changing tolerance widths over the lifetime of the radiation therapy device.

Design for MLC Position Correction in the Y Direction

In the currently existing radiation therapy devices in clinical use, the multi-leaf collimator (MLC) has no degree of freedom in the Y direction of the collimator coordinate system C. A possible redesign is shown in FIG. 1. For further explanation, the top view of FIG. 1 reproduces the side view and the bottom view reproduces the front view of the leaf packets.

To obtain this degree of freedom, the base plate collimator/MLC, which is the mechanical interface between the assembly of the lower jaws along with the assembly of the MLC and to which both units are firmly screwed, is modified. The new base plate consists of two layers that have a relative degree of freedom in the Y direction. The focus-side plate 3 is screwed to the assembly of the lower jaws 2a and 2b; the plate 5 on the isocenter side is screwed to the assembly of the MLC 7a and 7b.

Both plates are connected by means of two parallel linear guides 4a and 4b, which must allow only very small paths; a few millimeters are sufficient, which is the order of magnitude of the correction term $_c\Delta Y_{MLC}(G, C, T)$ in equation (21). The actuator for the dynamic or static, as the case may be, correction movement could be, for example, a piezo actuator 6, which can generate large forces at small paths and high velocities. It is firmly connected to the upper base plate 3 and acts on the lower base plate 5 via a rigid coupling.

In order for the correction paths or velocities, as the case may be, to be able to be precisely set and constantly monitored, such degree of freedom is provided with two independent path measuring systems. Linear encoders and/or potentiometers can be used for this purpose, for example. Thereby, a linear encoder can be integrated in the piezo actuator.

Design for Round Collimator Position Correction in the X and Y Directions

Figure 2:
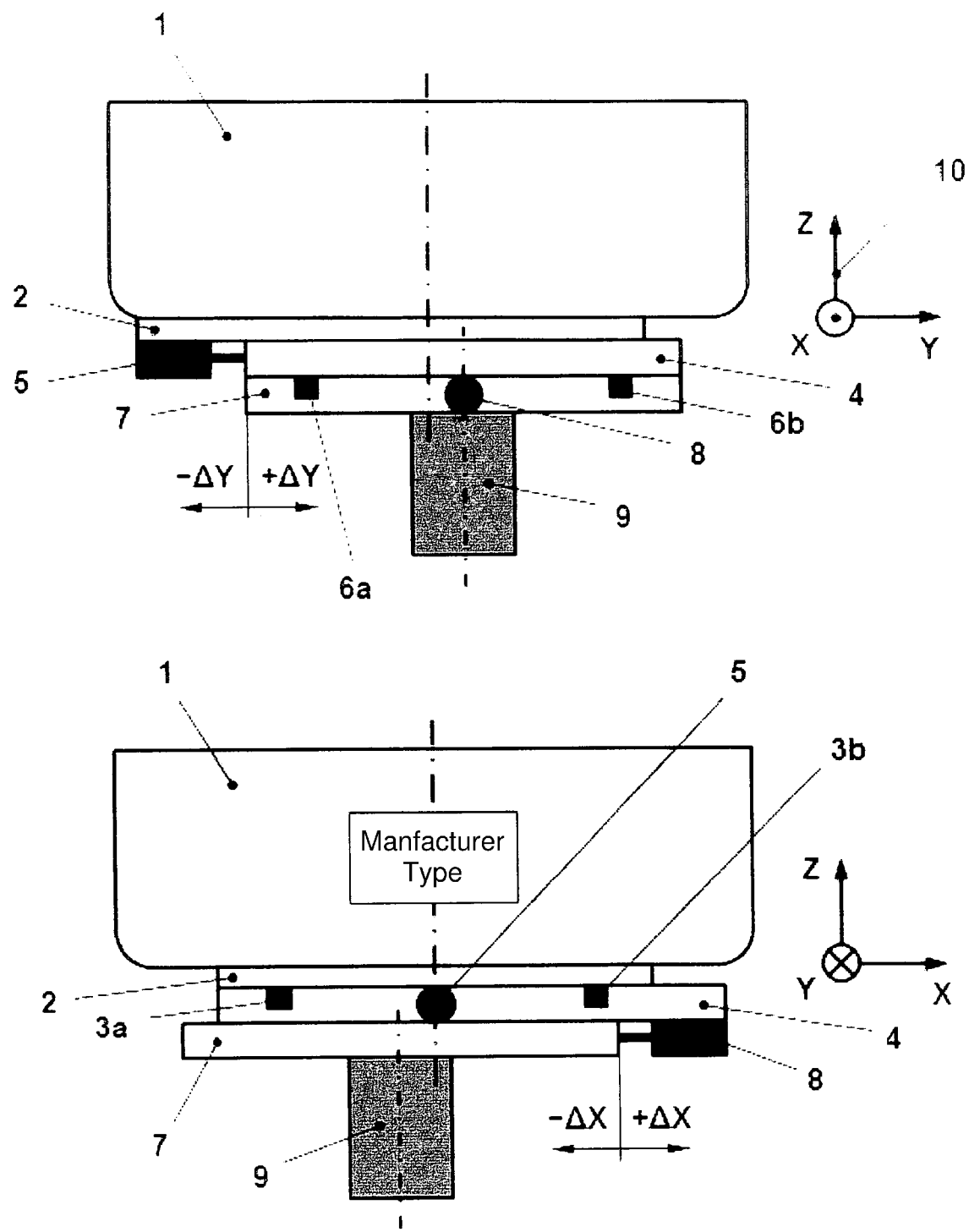
FIG. 2 shows a redesign of the degrees of freedom the X and Y directions for the round collimators.

In the currently existing radiation therapy devices in clinical use, the mounting of the round collimators on the radiator head has no degrees of freedom in the X and Y directions of the collimator coordinate system C. A possible embodiment of the redesign of both degrees of freedom is shown in FIG. 2. The side view is shown in the upper illustration and the front view is shown in the lower illustration of FIG. 2.

To realize the degrees of freedom, the base plate of the round collimator holder is divided into three parts:

The bracket with the upper base plate 2 is still firmly screwed to the radiator head 1. It is connected to the central part 4 via the linear guide pair 3a and 3b. The piezo actuator 5 is firmly connected to the upper part 2 and acts on the middle part 4 via a rigid coupling.

The central part 4 now has a degree of freedom in the Y direction relative to the upper part 2. A further piezo actuator 8 is in turn firmly connected to the central part 4 and acts via a rigid coupling on the lower part 7, which is movable relative to the central part 4 in the X direction with the aid of the linear guide pair 6a and 6b.

The lower part 7, which carries the round collimator 9 used, now has the additional degree of freedom in the X direction.

In FIG. 2, the Y degree of freedom is toward the radiator head side, and the X degree of freedom is toward the round collimator side. The local interchange of both degrees of freedom is also possible.

As already described in the previous section, each degree of freedom receives two independent path measuring systems, for example linear encoders and/or potentiometers.

Design for Position Correction of the Radiation Source in the Y Direction

With the currently existing radiation therapy devices in clinical use, the components of the radiation source target and compensating element have either one degree of freedom in the X direction or one degree of freedom in the Y direction of the source-fixed coordinate system S.

The procedure for obtaining the second degree of freedom is similar to the redesign of the Y degree of freedom of the multi-leaf collimator described above:

Modification of the carriage or carousel on which the respective component of the radiation source is arranged. Since the target and the compensating element each have a circular cross-section with a diameter of a few centimeters, an elongated hole with a specially dimensioned clearance fit is sufficient as a linear guide in the direction perpendicular to the existing degree of freedom, which is intended to hold the radiation source component in the direction of the existing degree of freedom with as little clearance as possible and to guide it slightly movably in the direction perpendicular thereto. For this purpose, the existing holes only have to be enlarged to elongated holes by means of milling.

A piezo actuator is attached to the carriage or carousel, as the case may be, of each radiation source component and acts on the respective component in the direction of the new degree of freedom via a rigid coupling.

An adjustment device for the piezo actuator about the Z axis of the source-fixed coordinate system S is more cost-effective than the clearance adjustment described above. This allows the direction of motion to be set at the factory exactly perpendicular to the existing degree of freedom without clearance via the rigid coupling between the piezo actuator and the moving component.

To ensure that the correction paths or velocities, as the case may be, can be precisely set and constantly monitored, each degree of freedom is equipped with two independent path measuring systems. Linear encoders and/or potentiometers can be used for this purpose, for example.

If a component $S_i$ of the radiation source is placed on a carousel, the position correction values to be applied to achieve those in equation (32) are functions of the angle of rotation $_K\gamma_K$ of the carousel about the Z axis of the carousel-fixed coordinate system K, which is parallel to that of the source-fixed coordinate system S, the additional radial degree of freedom $_K r_{P_i}$ due to the piezo actuator along with the correction terms in equation (32). If the axis of rotation of the carousel is arranged in the negative Y direction from the central beam, the radial correction value for the piezo actuator $P_i$ results in $$_K\Delta r_{P_i} = \frac{R_K \cdot (1 - \cos{_K\Delta_{\gamma K}}) + {_S\Delta Y_{S_i}}(G, C, T)}{\cos{_K\Delta_{\gamma K}}} \quad (39)$$

in the carousel-fixed coordinate system K, where $R_K$ is the carousel radius. The angle of rotation of the carousel required for setting the position correction in the circumferential direction is obtained in accordance with $$_K\Delta_{yK} = -\arcsin\left[\frac{s\Delta X_{S_i}(G, C, T)}{R_K + {_K\Delta r_{P_i}}}\right]. \quad (40)$$

Equations (39) and (40) form a nonlinear system of equations with interdependent variables $_K\Delta r_{P_i}$ and $_K\Delta\gamma_K$, representing polar coordinates. Substituting equation (39) into (40) yields a single nonlinear equation for the variable $_K\Delta\gamma_K$, which can be solved using Newton's iteration method. $_K\Delta r_{P_i}$ is in turn obtained by substituting the solution into equation (39). With the opposite position of the carousel axis of rotation, the equations for determining the correction terms of the piezo actuator are $$_K\Delta r_{P_i} = \frac{R_K \cdot (1 - \cos {_K\Delta_{yK}}) - s\Delta Y_{S_i}(G, C, T)}{\cos {_K\Delta_{yK}}} \text{ or} \quad (41)$$

$$_K\Delta_{yK} = \arcsin\left[\frac{s\Delta X_{S_i}(G, C, T)}{R_K + {_K\Delta r_{P_i}}}\right]. \quad (42)$$

Here, the extension by the additional degree of freedom in the Y direction was described. This design is also suitable for adding degrees of freedom in the X direction.

Accelerations During Patient Position Correction

The correction values determined using equation (35) can be applied directly by means of the drives of the translational table coordinates. The fact that this can be done safely for the patient is demonstrated on the basis of the velocities, accelerations and jolts (time derivatives of the acceleration components) of the patient positioning table calculated for a medical electron linear accelerator.

Figure 3:
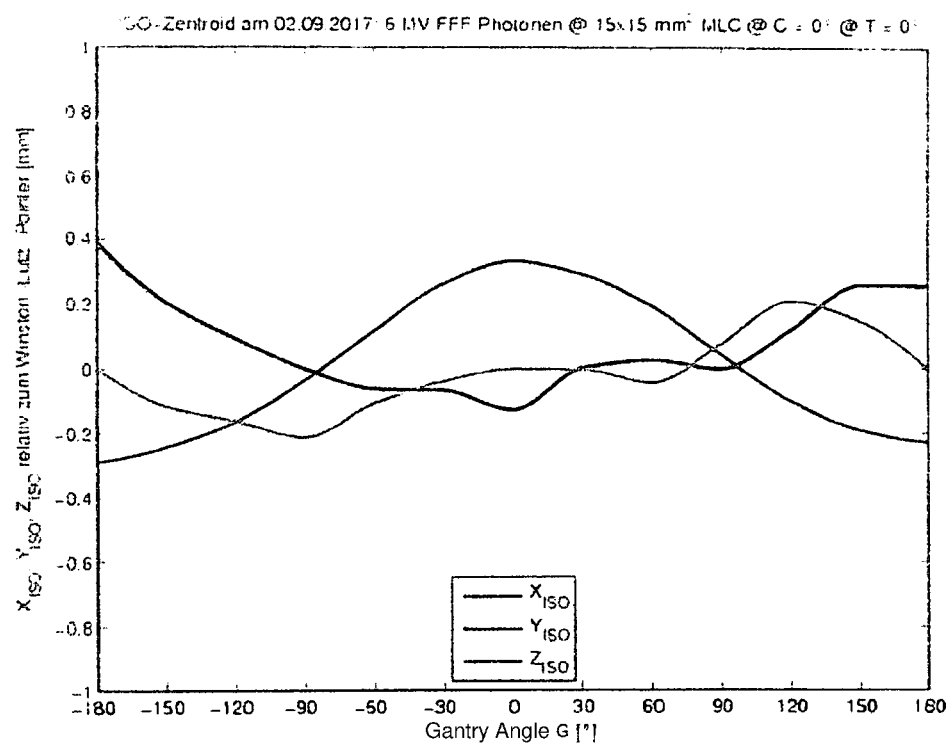
FIG. 3 shows illustrations of the deviations of the central beam position.

The illustration in FIG. 3 shows the spatial components of the central beam deviation of a medical electron linear accelerator as the support arm angle is varied throughout its range of values. Deviations of the spatial central beam position from the ideal isocenter of a medical electron linear accelerator of the model Novalis powered by TrueBeam™ STx manufactured by BRAINLAB AG (Feldkirchen, Germany) and VARIAN Medical Systems, Inc. (Palo Alto, CA, USA) during the variation of the support arm angle are shown. Calculation and graph generation were performed using the MATLAB® scientific computing software package, version R2007a (The MathWorks, Inc., Natick, MA, USA).

Figure 4:
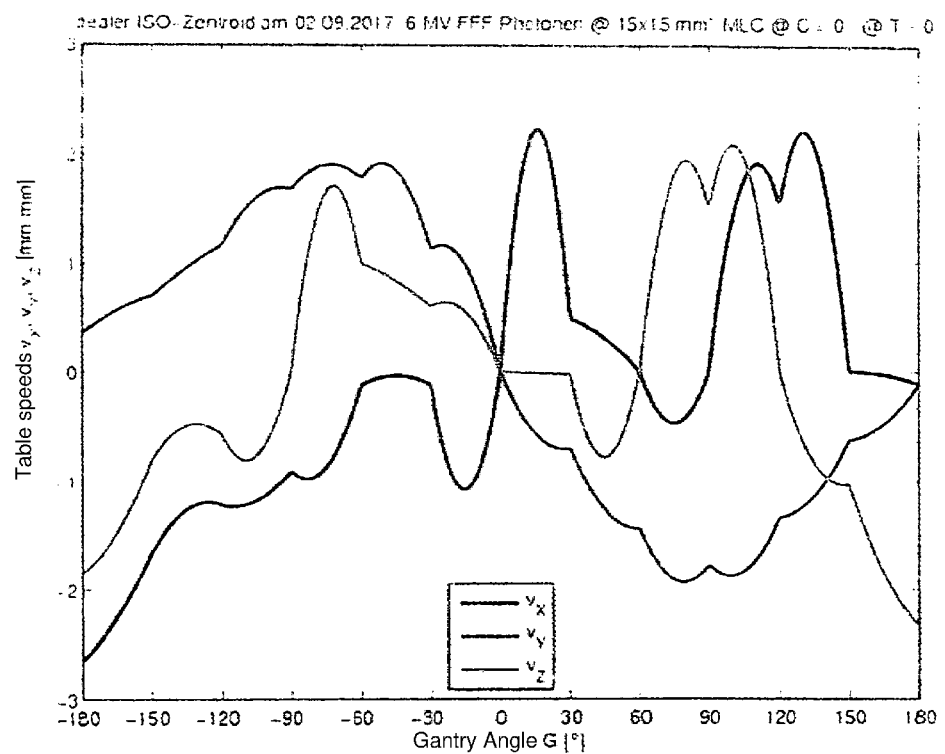
FIG. 4 shows translational velocity components of the patient positioning table.

FIG. 4 shows translational velocity components of the patient positioning table when correcting for patient positioning with the central beam deviations and at the maximum possible support arm angular velocity of 6°/s.

Calculation and graph generation was performed using MATLAB®, version R2007a.

As shown in FIG. 4, for a dynamic irradiation technique with the maximum possible support arm angular velocity 6°/s, all amounts of the velocity components are <3 mm/min. In comparison, patients are moved at velocities of up to 0.25 m/s=15 m/min during standard clinical position correction movements; that is, at 5000 times the velocity.

The components of the table accelerations have amounts <5 μm/s². On a patient with an average body mass of m=75 kg, the maximum inertial force would therefore amount to $$F_{max} = -m \cdot a_{max} = -75 \text{ kg} \cdot 5 \text{ μm/s}^2 = -0.375 \text{ mN} \quad (43)$$

A body with mass of 38 mg would experience a weight force of this amount. Deriving again with respect to time, one obtains the components of the table jolt, all of whose amounts are <2.5 μm/s³.

Figure 5:
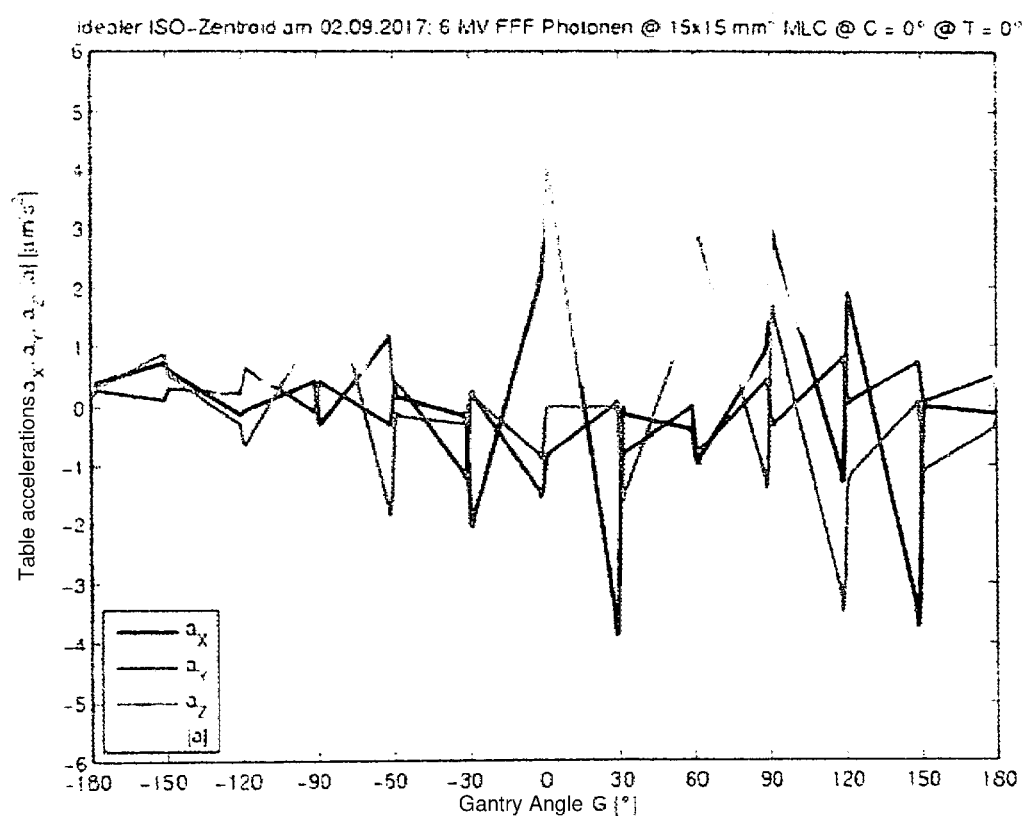
FIG. 5 shows translational acceleration components and resulting acceleration of the patient positioning table.

The graphical illustration of FIG. 5 shows the translational acceleration components and the resulting acceleration of the patient positioning table when correcting the patient position with the central beam deviations according to FIG. 3 and at the maximum possible support arm angular velocity of 6°/s. Calculation and graph generation was performed using MATLAB®, version R2007a.

Figure 6:
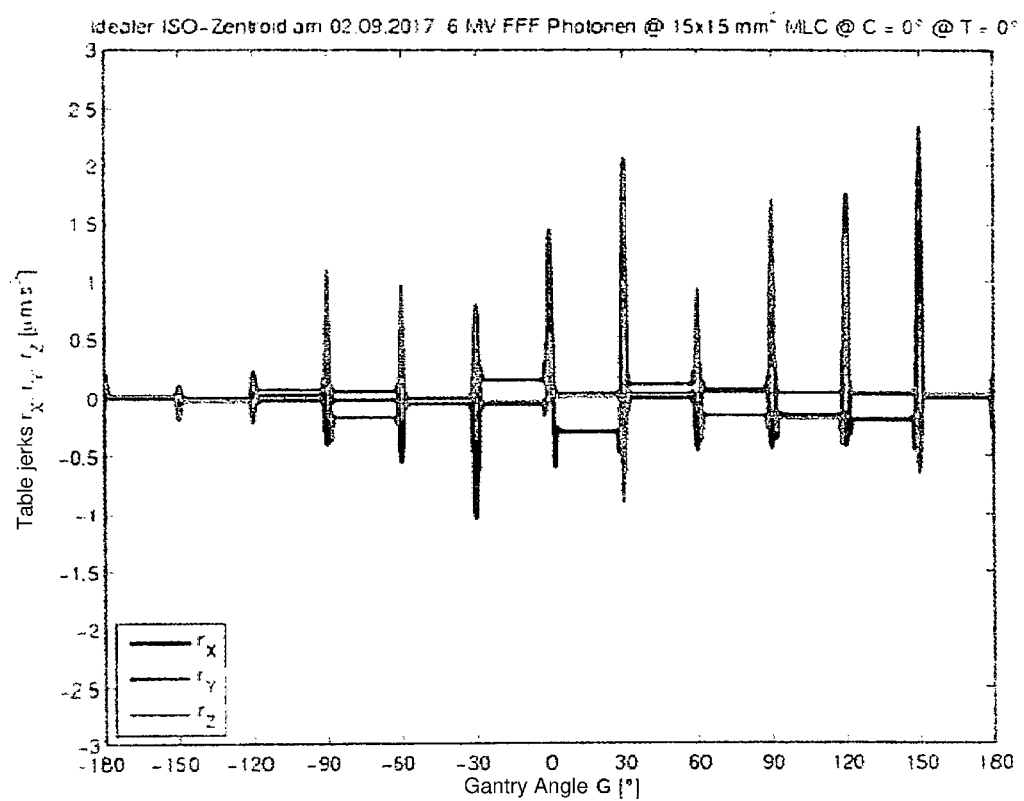
FIG. 6 shows translational jolt components of the patient positioning table during the correction of the patient position.
Figure 7:
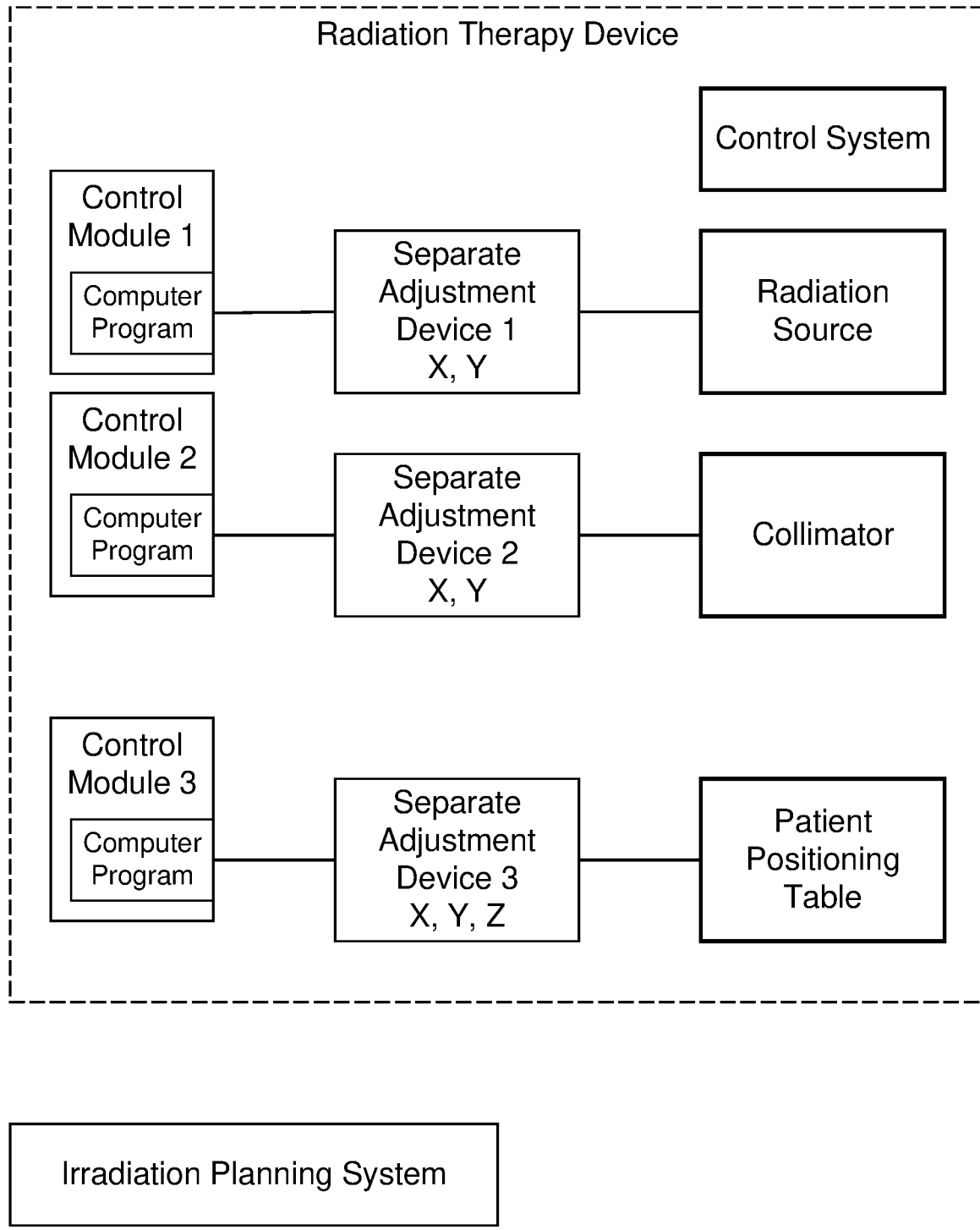
FIG. 7 is a block diagram showing components involved in a method for real-time related correction of a spatial position of a central beam of a radiation therapy device.

With the illustration of FIG. 6, the translational jolt components of the patient positioning table when correcting the patient position with the central beam deviations according to FIG. 3 are shown. Here as well, the support arm angular velocity amounts to 6°/s (worst case).

A patient on the patient positioning table would hardly feel the slight accelerations required for position correction. With good, reproducible positioning using suitable positioning aids, there is also no risk of relative movement between the patient and the positioning table top.

Application of the Corrective Movements in the Radiation Therapy Device

The application of the correction movements for geometric central beam correction by means of the collimator elements of block apertures, leaf packets and round collimators is possible both statically and dynamically. Their drives have dynamic capability; that is, they can execute defined time-dependent movements within the scope of their positioning accuracy. They each have a redundant path measuring system. The respective primary and secondary positions are constantly monitored. Only the angle-dependent or time-dependent, as the case may be, correction movements must be given to the drive controls of the collimator elements.

When using patient position correction, the translational table coordinate drives receive the motion commands. They also have redundant path measuring systems, whereby the above also applies. For radiation therapy devices not suitable for stereotactic radiotherapy and radiosurgery, only the positioning accuracy of the table coordinates would have to be increased by a factor of 10, so that path differences of <0.1 mm could be applied.

For a better understanding of the implementation of the correction movements, the control loops of the relevant drives are described in more detail below. Which control technology extensions are necessary for this is also discussed therein.

Control of the Drives

Modern radiation therapy devices have controlled drives that can move to statically as well as dynamically specified positions of translational and rotational degrees of freedom. The control mechanisms required for geometric central beam correction and patient position correction are now described here.

1. Positioning Accuracies

For example, the TrueBeam™ STx medical linear accelerator (Varian Medical Systems, Inc., Palo Alto, CA, USA), designed for radiosurgical applications, features drives with the positioning accuracies and velocity ranges summarized in Table 4. Their performance with regard to the required correction velocities in the order of magnitude of 3 mm/min=5·10⁻³ cm/s is many times greater and thus completely sufficient. However, their respective positioning accuracy would have to be improved by a factor of 5 . . . 10 for the implementation of the invention.

TABLE 4

Positioning accuracies, reproducibilities and velocity
ranges of the collimator and table
drives of an electron linear accelerator of the
model TrueBeam ™ STx.

| Component | Positioning Accuracy [mm] | Positioning Reproducability [mm] | Speed Range [cm/s] |
|---|---|---|---|
| X-block aperture | ±1 | ±0.5 | 0 . . . 2.5 |
| Y-block aperture | ±1 | ±0.5 | 0 . . . 2.5 |
| MLC carriage | ±1 | ±0.5 | 0 . . . 1.2 |
| MLC leaves | ±1 | ±0.5 | 0 . . . 2.5 |
| table X-axis | ±0.5 | ±0.5 | 0 . . . 3.5 |
| table Y-axis | ±0.5 | ±0.5 | 0 . . . 7 |
| table Z-axis | ±0.5 | ±0.5 | 0 . . . 2 |

2. Measuring Systems and Feedback of the Control Loops

All degrees of freedom required to correct the central beam deviations have redundant measuring systems as standard—one primary and one secondary—along ith their own closed-loop control circuit, wherein the position or velocity measured values, as the case may be, are fed back to the controller. Such feedback closest the control loop.

The measuring systems used in the TrueBeam™ STx electron linear accelerator are resolvers, encoders and potentiometers. Resolvers are electrical transducers that measure angles of rotation relative to a known physical position of a degree of freedom. Here, such reference position is a mechanical stop of the corresponding movement axis. Encoders convert rotatory or translational, as the case may be, positions into digital signals; they measure absolute positions. Potentiometers are electrical resistors whose values are linearly dependent on angle or path, as the case may be. The measuring systems used here are summarized in Table 5.

TABLE 5

Redundant measuring systems of the collimator
and table drives of an electron linear
accelerator of the model TrueBeam ™ STx.

| Component | primary system | secondary system | tertiary system |
|---|---|---|---|
| X-block aperture | Resolver | Resolver | — |
| Y-block aperture | Resolver | Resolver | — |
| MLC carriage | magnetic Encoder | optical Encoder | — |
| MLC leaves | magnetic Encoder | linear Potentiometer | — |
| table X-axis | Encoder | Encoder | Resolver |
| table Y-axis | Encoder | Encoder | Resolver |
| table Z-axis | absolute Potentiometer | absolute Potentiometer | Resolver |

3. Monitoring of the Drives

The primary sensors monitor the controlled drives. The feedback of the measuring signals in the respective control loop is used for the initialization and monitoring of the corresponding positioning and movement. When a targeted movement is made during a dynamic irradiation sequence, the main control program, referred to as a "supervisor" for short, automatically starts the associated movement. Thereby, the supervisor synchronizes the delivery of the absorbed dose with the motion. The cycle time of the control and synchronization amounts to 10 ms here.

If this time period is compared with the period of the temporal isocenter deviations, which amounts to approximately 30 s at a maximum support arm angular velocity (compare FIG. 3), it becomes clear that a correction of the isocenter deviations is possible in real time.

4. Sequence of Control Operations

After the irradiation plan with all parameters has been loaded from the radiation therapy device, the supervisor calculates the trajectories of all moving axes in terms of sequence, velocity and duration. The supervisor generates the commands for the data nodes of the drives, which are called "nodes." The commands are updated at intervals of 10 ms and include two future position values to be reached in a further 10 ms and 20 ms, as the case may be. The nodes in turn generate the motion specifications for the drives subordinate to them and require less than a time duration of 10 ms. Finally, this allows the drives to execute the required movements.

5. Communication Between Supervisor and Nodes

The data exchange takes place at each individual synchronization pulse. Every 10 ms, each node compares the position values received from the sensors with the respective target value. The supervisor checks the position values of the nodes and calculates two future position values for each. Three nodes are important for the implementation of the invention, which in the TrueBeam™ STx are called COL, CCHL and CCHU. They are responsible for the movements of all collimator elements, the vertical table coordinate (Z) and the lateral (X) and longitudinal table coordinate (Y), as the case may be.

6. Control Through Additionally Reinforcing Mechanisms

Here, the error detection capability of the redundant measuring systems is used. If necessary, adjustments are undertaken to correct positions, velocities and trajectories. This occurs in the respective node by comparing the supervisor's command with the current position of the primary sensor of the affected drive.

7. Necessary Extensions of the Control Loops

The controls of the drives for moving the block apertures, the MLC carriages and the leaves already have dynamic capability; in addition to positions, they can also control velocities. If one wishes to apply the proposed patient position correction, the control loops of all three table coordinates must be extended by one velocity control in each case. The same applies to the existing drives of the radiation source components; their control must be extended to include velocity control in each case.

To increase the positioning accuracy of all drives, the respective backlash should be reduced by modified machine elements. These are preloaded rolling bearings, recirculating ball screws, smaller tolerance widths for fits, and split pinions with spring preload. The path resolution of the sensors is sufficient; it is 0.1 mm relative to the isocenter plane.

Novelty

By using all geometric information regarding the precisely measured isocentroids of a radiation therapy device, one is able to calculate the correction terms for the beam-shaping collimator elements and/or for the translational degrees of freedom of the patient positioning table; this takes place offline by the irradiation planning system or online by the radiation therapy device. Such correction terms can be applied in real time during each irradiation session. One has no restrictions whatsoever in the selection of optimal irradiation parameters, a serious one of which is described in [2]; the collimator angle C=90°=const. is not always an optimal irradiation parameter.

Advantages

With the present invention, no expensive hardware solution is applied to further increase the support arm stiffness, so that the central beam position deviations become noticeably smaller. The support arm of an electron linear accelerator is a highly complex component that must accommodate many components of particle acceleration, beam generation, power supply and control technology. With a typical total component mass of 7.2 t, an optimum between component stiffness and dead weight has already been achieved.

The proposed solution makes it possible to correct the positional deviations between the real central beam and the tumor center during patient irradiation in real time, depending on the irradiation parameters of support arm angle, collimator angle and patient positioning table angle. With optimal radiation parameters from a radiooncological point of view, it is possible to deposit the absorbed dose in the focus of the disease with the highest possible geometric precision.

Used radiation therapy devices without a precise isocenter can achieve stereotaxy capability with the aid of the invention. In the future, radiation therapy devices with a support arm can once again be built more easily.

LITERATURE

[1] Dubbel—Pocketbook for Mechanical Engineering. 15th corrected and supplemented edition, edited by W. Beitz and K.-H. Küttner, Springer-Verlag, Berlin, Heidelberg, New York, Tokyo, 1986.
[2] Du, W., Gao, S., Wang, X., Kudchadker, R. J.: Quantifying the gantry sag on linear accelerators and introducing an MLC-based compensation strategy. Medical Physics, 39(4), 2156-2162, 2012.
[3] Pfeiffer, F., Glocker, Ch.: Multibody Dynamics with Unilateral Contacts. Series Editors: Ali H. Nayfeh and Arun V. Holden. John Wiley & Sons, Inc, New York, 1996.

REFERENCE SIGNS

1 Radiator head
1a Y1 block aperture
1b Y2 block aperture
2 Upper part of the round collimator holder
2a X1 block aperture
2b X2 block aperture
3 Upper part of the collimator/MLC base plate
3a Left-hand linear guide for the degree of freedom in the Y direction
3b Right-hand linear guide for the degree of freedom in the Y direction
4 Central part of the round collimator holder
4a Left-hand linear guide
4b Right-hand linear guide
5 Piezo actuator for movements ±ΔY
6 Piezo actuator for movements ±ΔY
6a Front-side linear guide for the degree of freedom in the X direction
6b Rear-side linear guide for the degree of freedom in the X direction
7 Lower part of the round collimator holder
7a Leaf packet of the B-side or X1-side, as the case may be
7b Leaf packet of the A-side or X2-side, as the case may be
8 Piezo actuator for movements ±ΔX
9 Round collimator
10 Collimator-fixed coordinate system C with the axes X, Y and Z
11 Lower part of the collimator/MLC base plate with the new degree of freedom in the Y direction

The invention claimed is:

1. A method for a real-time related correction of a spatial position of a central beam of a radiation therapy device by changing positions of collimator elements of a collimator and/or a spatial position of a patient support table, comprising:
retrofitting the radiation therapy device with
separate control modules, and
separate adjustment devices connected to the separate control modules, at least one of the separate adjustment devices being added to the collimator or the patient support table;
controlling the positions of the collimator elements and/or the spatial position of the patient support table for further degrees of freedom of movements, carried out through functional connections of the separate control modules;
changing the positions of the collimator elements and/or the spatial position of the patient support table within the further degrees of freedom, carried out via the separate adjustment devices; and
calculating correction movements in an irradiation planning system outside the radiation therapy device and/or in at least one microcontroller of a control system of the radiation therapy device.

2. The method according to claim 1,
wherein the controlling of the positions of the collimator elements and/or the spatial position of the patient support table is carried out by a respective one of the separate control modules, which is designed as a microcontroller, which contains a computer program controlling the separate adjustment devices.

3. The method according to claim 1,
wherein, by the separate control modules, the controlling of the positions of the collimator elements is affected within the further degrees of freedom in X and Y directions of a collimator-fixed coordinate system, and/or
wherein controlling the spatial position of the patient support table is affected within the further degrees of freedom in X, Y, and Z directions of a table-fixed coordinate system.

4. The method according to claim 1,
wherein the controlling of the positions of the collimator elements and/or the spatial position of the patient support table within the further degrees of freedom in X and Y directions is limited to a real-time related position change of the collimator elements.

5. The method according to claim 1,
wherein the controlling of the positions of the collimator elements and/or the spatial position of the patient support table within the further degrees of freedom in X, Y, and Z directions is limited to a real-time related change of the spatial position of the patient support table.

6. The method according to claim 1,
wherein the controlling of the positions of the collimator elements and/or the spatial position of the patient support table within the further degrees of freedom is affected by combined real-time related position changes of the collimator elements and the patient support table.

7. The method according to claim 1,
wherein the separate control modules are designed to be pre-adjustable according to an accuracy of changes of the positions of the collimator elements and/or of the spatial position of the patient support table, the further degrees of freedom, and/or a selection or a combination of the collimator elements and the patient support table to be controlled.

8. The method according to claim 1,
wherein controlling the positions of the collimator elements and/or the spatial position of the patient support table includes translational and/or rotatory degrees of freedom of movements of the positions of the collimator elements and/or the spatial position of the patient support table.

9. The method according to claim 1,
wherein the collimator is a multi-leaf collimator, the separate adjustment devices are piezo actuators, and the controlling the positions of the collimator elements of the multi-leaf collimator in a Y direction is carried out by the piezo actuators, or
wherein the collimator is a round collimator, the separate adjustment devices are piezo actuators, and the controlling the positions of the collimator elements of the round collimator in an X and a Y directions are carried out by the piezo actuators.

10. The method according to claim 1,
wherein a programming sequence and an interface of a computer program implemented in the irradiation planning system and/or the at least one microcontroller of the control system of the radiation therapy device are designed to be compatible with those of a main program of the radiation therapy device.

11. The method according to claim 1, further comprising:
changing a position of a radiation source within degrees of freedom in X and Y directions of a source-fixed coordinate system.

12. The method according to claim 1, further comprising:
changing a position of a radiation source in X and Y directions by one or more of the separate adjustment devices in form of piezo actuators.

13. The method according to claim 12,
wherein the radiation source is arranged on a carousel, and
wherein the changing the position of the radiation source is carried out by combined movements of the carousel and the piezo actuators.

14. The method according to claim 1,
wherein an electron beam is controlled by deflecting magnets and control coils synchronously with changes in a position of a target before striking the target, such that the electron beam always strikes a center of the target.

15. The method according to claim 1, further comprising:
simulating irradiation field limits in respective negative and positive X and Y directions of a collimator-fixed coordinate system by the collimator elements.

* * * * *